(12) United States Patent
Schmidt et al.

(10) Patent No.: US 7,671,050 B2
(45) Date of Patent: Mar. 2, 2010

(54) TRIAZOLOPHTHALAZINES

(75) Inventors: Beate Schmidt, Allensbach (DE);
Steffen Weinbrenner, Constance (DE);
Dieter Flockerzi, Allensbach (DE);
Raimund Külzer, Radolfzell (DE);
Hermann Tenor, Radolfzell (DE);
Hans-Peter Kley, Allensbach (DE)

(73) Assignee: NYCOMED GmbH, Constance (DE)

( * ) Notice: Subject to any disclaimer, the term of this patent is extended or adjusted under 35 U.S.C. 154(b) by 82 days.

(21) Appl. No.: 11/794,129

(22) PCT Filed: Jan. 4, 2006

(86) PCT No.: PCT/EP2006/050032

§ 371 (c)(1),
(2), (4) Date: Aug. 22, 2007

(87) PCT Pub. No.: WO2006/072612

PCT Pub. Date: Jul. 13, 2006

(65) Prior Publication Data

US 2008/0280907 A1    Nov. 13, 2008

(30) Foreign Application Priority Data

Jan. 5, 2005    (EP) .................... 05100043

(51) Int. Cl.
A61K 31/5025    (2006.01)
A61K 31/5377    (2006.01)
C07D 487/04    (2006.01)
C07D 237/34    (2006.01)
A61P 25/00    (2006.01)
A61P 9/06    (2006.01)

(52) U.S. Cl. .................... 514/233.2; 514/248; 544/234; 544/115; 544/237

(58) Field of Classification Search ............. 514/228.5, 514/233.2, 248; 544/60, 115, 234
See application file for complete search history.

(56) References Cited

U.S. PATENT DOCUMENTS

| 6,001,830 | A | 12/1999 | Lee et al. |
| 6,235,741 | B1 | 5/2001 | Bilodeau et al. |
| 6,313,125 | B1 | 11/2001 | Carling et al. |
| 6,525,055 | B1 | 2/2003 | Napoletano et al. |
| 6,900,209 | B2 | 5/2005 | Chambers et al. |

FOREIGN PATENT DOCUMENTS

| EP | 0 085 840 A1 | 8/1983 |
| EP | 0 728 759 A1 | 8/1996 |
| WO | 98/04559 A2 | 2/1998 |
| WO | 98/50385 A1 | 11/1998 |
| WO | 99/06407 A1 | 2/1999 |
| WO | 00/26218 A1 | 5/2000 |
| WO | 01/47929 A1 | 7/2001 |
| WO | 02/083140 A1 | 10/2002 |
| WO | 2004/022062 A1 | 3/2004 |
| WO | 2004/087707 A1 | 10/2004 |
| WO | 2006/024640 A2 | 3/2006 |
| WO | 2006/072615 A2 | 7/2006 |

OTHER PUBLICATIONS

Pieretti, et al., Life Sciences, vol. 79, # 8, Jul. 17, 2006, 791-800.*
Marx, et al., Pulmon. Pharmacol. & Therap., vol. 15, # 1, Jan. 2002, pp. 7-15.*
Velardez, et al., Europ. J. Endocrin., 2000, 143, 279-284.*
Lugnier, Pharmacol. & Therap., vol. 109, # 3, Mar. 2006, pp. 366-398.*
Carling, R.W., et al., "3-Phenyl-6-(2-pyridyl)methyloxy-1,2,4-triazolo[3,4-a]phthalazines and Analogues: High-Affinity γ-Aminobutyric Acid-A Benzodiazepine Receptor Ligands with α2, α3, and α5-Subtype Binding Selectivity over α1", J. Med. Chem., vol. 47, pp. 1807-1822, (2004).
Sternfeld, F., et al., "Selective, Orally Active γ-Aminobutyric Acid$_A$ α5 Receptor Inverse Agonists as Cognition Enhancers", J. Med. Chem., vol. 47, pp. 2176-2179, (2004).
Tarzia, G., et al., "6-(Alkylamino)-3-aryl-1,2,4-triazolo[3,4-a]phthalazines. A New Class of Benzodiazepine Receptor Ligands", J. Med. Chem., vol. 31, pp. 1115-1123, (1988).
Seybold, J. et al., "Tumor necrosis factor-{alpha}-dependent expression of phosphodiesterase 2: role in endothelial hyperpermeability," Blood, vol. 105, pp. 3569-3576 (prepublished online Jan. 13, 2005).
Witzenrath M. et al., "Phosphodiesterase 2 inhibition diminished acute lung injury in murine pneumococcal pneumonia," Critical Care Medicine, vol. 37, No. 2, pp. 1-7 (2009).
Netherton, S.J. et al., "Vascular Endothelial Cell Cyclic Nucleotide Phosphodiesterases and Regulated Cell Migration: Implications in Angiogenesis," Molecular Pharmacology, vol. 67, pp. 263-272 (2005).
Favot L. et al., "VEGF-induced HUVEC migration and proliferation are decreased by PDE2 and PDE4 inhibitors," Journal of Thrombosis and Haemostasis, vol. 90, pp. 334-343, (2003).

* cited by examiner

Primary Examiner—Mark L Berch
Assistant Examiner—Cecilia M Jaisle
(74) Attorney, Agent, or Firm—The Nath Law Group; Joshua B. Goldberg; Sheldon M. McGee

(57) ABSTRACT

The compounds of formula (I)

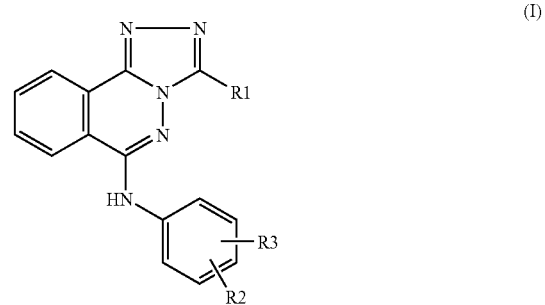

in which R1, R2 and R3 have the meanings as given in the description are novel effective PDE2 inhibitors.

6 Claims, No Drawings

```
                        SEQUENCE LISTING

<160> NUMBER OF SEQ ID NOS: 4

<210> SEQ ID NO 1
<211> LENGTH: 19
<212> TYPE: DNA
<213> ORGANISM: Artificial
<220> FEATURE:
<221> NAME/KEY: Primer
<222> LOCATION: (1)..(19)
<223> OTHER INFORMATION: Primer CP1PD2AS

<400> SEQUENCE: 1
gaggagtgat ggggcaggc                                                    19

<210> SEQ ID NO 2
<211> LENGTH: 21
<212> TYPE: DNA
<213> ORGANISM: Artificial
<220> FEATURE:
<221> NAME/KEY: Primer
<222> LOCATION: (1)..(21)
<223> OTHER INFORMATION: Primer PR9PD2AA

<400> SEQUENCE: 2
gcgaagtggg agacagaaaa g                                                 21

<210> SEQ ID NO 3
<211> LENGTH: 20
<212> TYPE: DNA
<213> ORGANISM: Artificial
<220> FEATURE:
<221> NAME/KEY: Primer
<222> LOCATION: (1)..(20)
<223> OTHER INFORMATION: Primer PR7PD2AS

<400> SEQUENCE: 3
```

```
gatcctgaac atccctgacg                                            20

<210> SEQ ID NO 4
<211> LENGTH: 21
<212> TYPE: DNA
<213> ORGANISM: Artificial
<220> FEATURE:
<221> NAME/KEY: Primer
<222> LOCATION: (1)..(21)
<223> OTHER INFORMATION: Primer CP3PD2AA

<400> SEQUENCE: 4
gggatcactc agcatcaagg c                                          21
```

TRIAZOLOPHTHALAZINES

This application was filed under 35 U.S.C. 371 as a national stage of PCT/EP2006/050032, filed Jan. 4, 2006.

FIELD OF APPLICATION OF THE INVENTION

The invention relates to novel triazolophthalazine derivatives, which can be used in the pharmaceutical industry for the production of pharmaceutical compositions.

KNOWN TECHNICAL BACKGROUND

Triazolophthalazines are known from prior art. For example, EP85840, WO98/04559, WO98/50385, WO99/06407 (corresponding to U.S. Pat. No. 6,313,125), WO02/083140, WO00/26218 (corresponding to U.S. Pat. No. 6,525,055), EP0728759 (corresponding to U.S. Pat. No. 6,001,830); J. Med. Chem., (1988), 31, 1115-1123; J. Med. Chem., (2004), 47, 1807-1822, and J. Med. Chem., (2004), 47, 2176-2179 describe triazolophthalazines with various substitution patterns.

But, however, anilino-substituted triazolophthalazine derivatives in the meaning of the present invention have never been disclosed therein.

WO01/47929 describes triazolotriazinones with PDE2 inhibiting activity.

Yet however, triazolophthalazine derivatives have never been described as PDE2-inhibitors.

DESCRIPTION OF THE INVENTION

It has now been found that the novel triazolophthalazine derivatives, which are described in greater details below, have surprising and particularly advantageous properties.

The invention thus relates to compounds of formula I

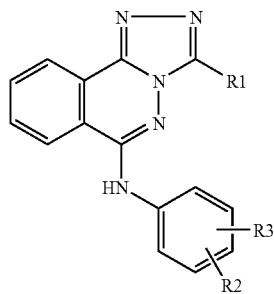

in which
R1 is —U-A, in which
U is a direct bond, or methylene (—CH$_2$—),
A is phenyl, pyridinyl, thiophenyl, or R11- and/or R111-substituted phenyl, in which
R11 is 1-4C-alkyl, halogen, trifluoromethyl, hydroxyl, 1-4C-alkoxy, completely or predominantly fluorine-substituted 1-4C-alkoxy, phenoxy, 1-4C-alkoxycarbonyl, morpholino, or di-1-4C-alkylamino,
R111 is 1-4C-alkoxy, halogen, hydroxyl, or 1-4C-alkyl,
R2 is hydrogen, 1-4C-alkyl, 1-4C-alkoxy, phenyl-1-4C-alkoxy, phenoxy, 3-7C-cycloalkoxy, 3-7C-cycloalkylmethoxy, halogen, trifluoromethyl, nitro, phenyl, R21-substituted phenyl, completely or predominantly fluorine-substituted 1-4C-alkoxy, 1-4C-alkylthio, cyano-1-4C-alkyl, or —N(R22)R23, in which
R21 is 1-4C-alkoxy, halogen or 1-4C-alkyl,
R22 and R23 together and with inclusion of the nitrogen atom, to which they are attached, form a heterocyclic ring Het1, in which
Het1 is optionally substituted by R24, and is a 3- to 7-membered monocyclic fully saturated heterocyclic ring radical comprising the nitrogen atom, to which R22 and R23 are bonded, and optionally one further heteroatom selected from nitrogen, oxygen and sulphur, in which
R24 is 1-4C-alkyl,
R3 is hydrogen, 1-4C-alkyl, 1-4C-alkoxy or halogen, and the salts of these compounds.

1-4C-Alkyl is a straight-chain or branched alkyl radical having 1 to 4 carbon atoms. Examples are the butyl, isobutyl, sec-butyl, tert-butyl, propyl, isopropyl, and, particularly, the ethyl and methyl radicals.

Halogen within the meaning of the present invention is iodine or, in particular, bromine, chlorine or fluorine.

1-4C-Alkoxy represents radicals which, in addition to the oxygen atom, contain a straight-chain or branched alkyl radical having 1 to 4 carbon atoms. Examples which may be mentioned are the butoxy, isobutoxy, sec-butoxy, tert-butoxy, propoxy, isopropoxy and, particularly, the ethoxy and methoxy radicals.

1-4C-Alkoxycarbonyl is a carbonyl group to which one of the abovementioned 1-4C-alkoxy radicals is bonded. Examples are the methoxycarbonyl (CH$_3$O—C(O)—) and the ethoxycarbonyl (CH$_3$CH$_2$O—C(O)—) radical.

3-7C-Cycloalkylmethoxy stands for cyclopropylmethoxy, cyclobutylmethoxy, cyclopentylmethoxy, cyclohexylmethoxy or cycloheptylmethoxy, of which cyclopropylmethoxy and cyclopentylmethoxy are to be emphasized.

3-7C-Cycloalkoxy represents cyclopropyloxy, cyclobutyloxy, cyclopentyloxy, cyclohexyloxy and cycloheptyloxy, of which cyclopropyloxy, cyclobutyloxy and cyclopentyloxy are preferred.

Completely or predominantly fluorine-substituted 1-4C-alkoxy is, for example, the 2,2,3,3,3-pentafluoropropoxy, the perfluoroethoxy, the 1,2,2-trifluoroethoxy and in particular the 1,1,2,2-tetrafluoroethoxy, the 2,2,2-trifluoroethoxy, the trifluoromethoxy and the difluoromethoxy radical, of which the difluoromethoxy radical is preferred. "Predominantly" in this connection means that more than half of the hydrogen atoms of the 1-4C-alkoxy groups are replaced by fluorine atoms.

Di-1-4C-alkylamino stands for an amino group, which is substituted by two different or two identical of the abovementioned 1-4C-alkyl radicals. Examples are the dimethylamino, the diethylamino and the diisopropyl radical.

Di-(1-4C-alkoxy)-phenyl stands for a phenyl radical, which is substituted at any possible positions by two of the abovementioned 1-4C-alkoxy radicals, which may be the same or different.

Phenyl-1-4C-alkoxy stands for one of the abovementioned 1-4C-alkoxy radicals, which is substituted by the phenyl radical. Examples which may be mentioned are the benzyloxy and the phenethoxy radical.

Cyano-1-4C-alkyl stands for one of the abovementioned 1-4C-alkyl radicals, which is substituted by the cyano group. Examples which may be mentioned are the cyanomethyl and the 2-cyanoethyl radical.

4N-(1-4C-Alkyl)-piperazin-1-yl stands for a piperazine-1-yl radical which is substituted at its nitrogen atom in the 4-position by one of the abovementioned 1-4C-alkyl radicals, such as e.g. 4N-methyl-piperazin-1-yl.

1-4C-Alkylthio represents radicals which, in addition to the sulfur atom, contain one of the abovementioned 1-4C-alkyl radicals. Examples which may be mentioned are the butylthio, propylthio and preferably the ethylthio and methylthio radicals.

In the meaning of the present invention, it is to be understood, that, when two structural portions of the compounds according to this invention are linked via a constituent which has the meaning "bond", then said two portions are directly attached to another via a single bond.

Het1 is optionally substituted by R24, and is a 3- to 7-membered monocyclic fully saturated heterocyclic ring radical comprising the nitrogen atom, to which R22 and R23 are bonded, and optionally one further heteroatom selected from nitrogen, oxygen and sulphur.

In an embodiment, Het1 stands for a 3- to 7-membered monocyclic fully saturated heterocyclic ring radical comprising the nitrogen atom, to which R22 and R23 are bonded, and optionally one further heteroatom selected from NH, N(R24), oxygen and sulphur.

Het1 may include, for example, without being restricted thereto, aziridin-1-yl, azetidin-1-yl, pyrrolidin-1-yl, piperidin-1-yl, homopiperidin-1-yl, morpholin-4-yl, thiomorpholin-4-yl, piperazin-1-yl and homopiperazin-1-yl.

As further examples for Het1 according to this invention may be mentioned, without being restricted thereto, R24-substituted derivatives of the abovementioned exemplary Het1 radicals, such as e.g. 4N-(R24)-piperazin-1-yl or 4N-(R24)-homopiperazin-1-yl.

Illustratively, as exemplary suitable Het1 radical may be mentioned, without being restricted thereto, 4N-(1-4C-alkyl)-piperazin-1-yl, such as e.g. 4N-methyl-piperazin-1-yl, or, particularly, morpholin-4-yl.

The heterocyclic groups mentioned herein refer, unless otherwise mentioned, to all of the possible isomeric forms thereof.

The heterocyclic groups mentioned herein refer, unless otherwise noted, in particular to all of the possible positional isomers thereof. Such as, for example, the terms pyridyl or pyridinyl, alone or as part of another group, include pyridin-2-yl, pyridin-3-yl and pyridin-4-yl, or the term thiophenyl includes thiophen-2-yl and thiophen-3-yl.

Constituents, which are substituted as stated herein, may be substituted, unless otherwise noted, at any possible position.

The heterocyclic groups mentioned herein may be substituted by their given substituents, unless otherwise noted, at any possible position, such as e.g. at any substitutable ring carbon or ring nitrogen atom.

Unless otherwise noted, any heteroatom of a heterocyclic ring with unsatisfied valences mentioned herein is assumed to have the hydrogen atom(s) to satisfy the valences.

When any variable occurs more than one time in any constituent, each definition is independent.

The substituents R2 and R3 of compounds of formula I can be attached in the ortho, meta or para position with respect to the binding position in which the phenyl ring is bonded to the amino group, whereby preference is given to the attachment in the meta or para position.

Suitable salts for compounds according to this invention—depending on substitution—are all acid addition salts or all salts with bases. Particular mention may be made of the pharmacologically tolerable inorganic and organic acids and bases customarily used in pharmacy. Those suitable are, on the one hand, water-insoluble and, particularly, water-soluble acid addition salts with acids such as, for example, hydrochloric acid, hydrobromic acid, phosphoric acid, nitric acid, sulphuric acid, acetic acid, citric acid, D-gluconic acid, benzoic acid, 2-(4-hydroxybenzoyl)benzoic acid, butyric acid, sulphosalicylic acid, maleic acid, lauric acid, malic acid, fumaric acid, succinic acid, oxalic acid, tartaric acid, embonic acid, stearic acid, toluenesulphonic acid, methanesulphonic acid or 3-hydroxy-2-naphthoic acid, the acids being employed in salt preparation—depending on whether a mono- or polybasic acid is concerned and depending on which salt is desired—in an equimolar quantitative ratio or one differing therefrom.

On the other hand, salts with bases are—depending on substitution—also suitable. As examples of salts with bases are mentioned the lithium, sodium, potassium, calcium, aluminium, magnesium, titanium, ammonium, meglumine or guanidinium salts, here, too, the bases being employed in salt preparation in an equimolar quantitative ratio or one differing therefrom.

Pharmacologically intolerable salts, which can be obtained, for example, as process products during the preparation of the compounds according to this invention on an industrial scale, are converted into pharmacologically tolerable salts by processes known to the person skilled in the art.

According to expert's knowledge the compounds according to this invention as well as their salts may contain, e.g. when isolated in crystalline form, varying amounts of solvents. Included within the scope of the invention are therefore all solvates and in particular all hydrates of the compounds according to this invention as well as all solvates and in particular all hydrates of the salts of the compounds according to this invention.

Compounds according to this invention worthy to be mentioned are those compounds of formula I, in which R1 is —U-A, in which U is a direct bond, or methylene (—CH$_2$—), A is phenyl, pyridinyl, thiophenyl, di-(1-4C-alkoxy)-phenyl, or R11-substituted phenyl, in which R11 is 1-4C-alkyl, halogen, trifluoromethyl, hydroxyl, 1-4C-alkoxy, completely or predominantly fluorine-substituted 1-4C-alkoxy, phenoxy, 1-4C-alkoxycarbonyl, morpholino, or di-1-4C-alkylamino, R2 is hydrogen, 1-4C-alkyl, 1-4C-alkoxy, phenyl-1-4C-alkoxy, phenoxy, 3-7C-cycloalkoxy, 3-7C-cycloalkyl-methoxy, halogen, phenyl, R21-substituted phenyl, completely or predominantly fluorine-substituted 1-4C-alkoxy, 1-4C-alkylthio, cyano-1-4C-alkyl, or —N(R22)R23, in which R21 is 1-4C-alkoxy, halogen or 1-4C-alkyl, R22 and R23 together and with inclusion of the nitrogen atom, to which they are attached, form a heterocyclic ring Het1, in which Het1 is a 3- to 7-membered monocyclic fully saturated heterocyclic ring radical comprising the nitrogen atom, to which R22 and R23 are bonded, and optionally one further heteroatom selected from N(R24), oxygen or sulphur, in which R24 is 1-4C-alkyl, R3 is hydrogen, 1-4C-alkyl, 1-4C-alkoxy or halogen, and the salts of these compounds.

Compounds according to this invention more worthy to be mentioned are those compounds of formula I, in which R1 is —U-A, in which U is a direct bond, or methylene (—CH$_2$—), A is phenyl, pyridinyl, thiophenyl, dimethoxyphenyl, or R11-substituted phenyl, in which R11 is methyl, tertbutyl, chlorine, fluorine, bromine, trifluoromethyl, hydroxyl, methoxy, ethoxy, trifluoromethoxy, phenoxy, methoxycarbonyl, morpholino, or dimethylamino, R2 is hydrogen, 1-4C-alkyl, 1-4C-alkoxy, phenyl-1-4C-alkoxy, phenoxy, halogen, phenyl, R21-substituted phenyl, completely or predominantly fluorine-substituted 1-4C-alkoxy, 1-4C-alkylthio, cyano-1-4C-alkyl, or —N(R22)R23, in which R21 is 1-4C-alkoxy, R22 and R23 together and with inclusion of the nitrogen atom, to which they are attached, form a heterocyclic ring Het1, in which Het1 is pyrrolidin-1-yl, piperidin-1-yl, morpholin-4-yl, thiomorpholin-4-yl, or 4N-(1-4C-alkyl)-piperazin-1-yl, R3 is hydrogen or 1-4C-alkoxy, and the salts of these compounds.

Compounds according to this invention in particular worthy to be mentioned are those compounds of formula I, in which R1 is —U-A, in which U is a direct bond, or methylene (—CH$_2$—), A is phenyl, or R11-substituted phenyl, in which R11 is methyl, chlorine, fluorine, bromine, trifluoromethyl, hydroxyl, methoxy, phenoxy, methoxycarbonyl, or dimethylamino, whereby in particular A is 4-methoxy-phenyl, 2-methoxy-phenyl, 2-bromo-phenyl, 4-bromo-phenyl, 2-fluoro-phenyl, 2-(trifluoromethyl)-phenyl, 3-methoxy-phenyl, 3-bromo-phenyl, 3-fluoro-phenyl, or 3-(trifluoromethyl)-phenyl;

R2 is hydrogen, 1-4C-alkyl, 1-4C-alkoxy, phenyl-1-4C-alkoxy, phenoxy, halogen, phenyl, R21-substituted phenyl, completely or predominantly fluorine-substituted 1-4C-alkoxy, 1-4C-alkylthio, cyano-1-4C-alkyl, or —N(R22)R23, in which R21 is 1-4C-alkoxy, R22 and R23 together and with inclusion of the nitrogen atom, to which they are attached, form a heterocyclic ring Het1, in which Het1 is morpholin-4-yl, or 4N-(1-4C-alkyl)-piperazin-1-yl, R3 is hydrogen or 1-4C-alkoxy, and the salts of these compounds.

Compounds of formula I according to claim 1, in which

R1 is —U-A, in which

U is a direct bond, or methylene (—CH$_2$—),

A is phenyl, 4-methoxy-phenyl, 2-methoxy-phenyl, 2-hydroxy-phenyl, 2-bromo-phenyl, 4-bromo-phenyl, 2-fluoro-phenyl, 2-(trifluoromethyl)-phenyl, 2-methyl-phenyl, 3-methoxy-phenyl, 3-bromo-phenyl, 3-fluoro-phenyl, 2-dimethylamino-phenyl, methoxycarbonyl, phenoxy, or 3-(trifluoromethyl)-phenyl R2 is hydrogen, 1-4C-alkyl, 1-4C-alkoxy, phenyl-1-4C-alkoxy, phenoxy, halogen, phenyl, R21-substituted phenyl, completely or predominantly fluorine-substituted 1-4C-alkoxy, 1-4C-alkylthio, cyano-1-4C-alkyl, or —N(R22)R23, in which R21 is 1-4C-alkoxy, R22 and R23 together and with inclusion of the nitrogen atom, to which they are attached, form a heterocyclic ring Het1, in which Het1 is morpholin-4-yl, or 4N-(1-4C-alkyl)-piperazin-1-yl, R3 is hydrogen or 1-4C-alkoxy, and the salts of these compounds.

Compounds according to this invention in more particular worthy to be mentioned are those compounds of formula I, in which R1 is —U-A, in which U is a direct bond, A is phenyl, or R11-substituted phenyl, in which R11 is fluorine, bromine, trifluoromethyl, or methoxy, whereby in particular R1 is 4-methoxy-phenyl, 2-methoxy-phenyl, 3-methoxy-phenyl, 2-bromo-phenyl, 3-bromo-phenyl, 4-bromo-phenyl, 2-fluoro-phenyl, 3-fluoro-phenyl, 2-(trifluoromethyl)-phenyl, or 3-(trifluoromethyl)-phenyl, and whereby in more particular R1 is 4-methoxy-phenyl, or 2-bromo-phenyl;

R2 is hydrogen, methyl, methoxy, ethoxy, benzyloxy, chlorine, phenoxy, phenyl, 4-methoxyphenyl, trifluoromethoxy, difluoromethoxy, methylthio, cyanomethyl, or —N(R22)R23, in which R22 and R23 together and with inclusion of the nitrogen atom, to which they are attached, form a heterocyclic ring Het1, in which Het1 is morpholin-4-yl, or 4N-methyl-piperazin-1-yl, R3 is hydrogen, methoxy or ethoxy, and the salts of these compounds.

Compounds of formula I according to claim 1, in which

R1 is 4-methoxy-phenyl, 2-methoxy-phenyl, 3-methoxy-phenyl, 2-bromo-phenyl, 3-bromo-phenyl, 4-bromo-phenyl, 2-fluoro-phenyl, 3-fluoro-phenyl, 2-(trifluoromethyl)-phenyl, or 3-(trifluoromethyl)-phenyl;

R2 is hydrogen, methyl, methoxy, ethoxy, benzyloxy, chlorine, phenoxy, phenyl, 4-methoxyphenyl, trifluoromethoxy, difluoromethoxy, methylthio, cyanomethyl, or —N(R22)R23, in which R22 and R23 together and with inclusion of the nitrogen atom, to which they are attached, form a heterocyclic ring Het1, in which Het1 is morpholin-4-yl, or 4N-methyl-piperazin-1-yl, R3 is hydrogen, methoxy or ethoxy, and the salts of these compounds.

Compounds of formula I according to claim 1, in which

R1 is phenyl, 2-hydroxy-phenyl, 4-phenoxy-phenyl, 3-methoxy-carbonyl-phenyl, 4-methoxycarbonyl-phenyl, 4-morpholin-4-yl-phenyl, 4-methoxy-benzyl, R2 is —N(R22)R23, in which R22 and R23 together and with inclusion of the nitrogen atom, to which they are attached, form a heterocyclic ring Het1, which is morpholin-4-yl, R3 is hydrogen, and the salts of these compounds.

Compounds of formula I according to claim 1, in which

R1 is 4-methoxy-phenyl,

R2 is hydrogen, methyl, methoxy, ethoxy, phenyl-methoxy, phenoxy, chloro, bromo, R21-substituted phenyl, trifluoromethoxy, difluoromethoxy, methylthio, cyano-1-4C-alkyl, or —N(R22)R23, in which R21 is methoxy, R22 and R23 together and with inclusion of the nitrogen atom, to which they are attached, form a heterocyclic ring Het1, which is morpholin-4-yl, or 4N-methyl-piperazin-1-yl, R3 is hydrogen, and the salts of these compounds.

Compounds of formula I according to claim 1, in which
R1 is 4-methoxy-phenyl,
R2 and R3 is methoxy or ethoxy.

and the salts of these compounds.

A special interest in the compounds according to this invention refers to those compounds of formula I which are included—within the scope of this invention—by one or, when possible, by more of the following special embodiments:

A special embodiment (embodiment 1) of the compounds according to the present invention refers to those compounds of formula I, in which
U is a direct bond, and
A is phenyl, or R11-substituted phenyl.

Another special embodiment (embodiment 2) of the compounds according to the present invention refers to those compounds of formula I, in which
U is a direct bond, and
A is pyridinyl or thiophenyl, such as e.g. pyridin-4-yl.

Another special embodiment (embodiment 3) of the compounds according to the present invention refers to those compounds of formula I, in which
U is methylene, and
A is phenyl, or R11-substituted phenyl.

Another special embodiment (embodiment 4) of the compounds according to the present invention refers to those compounds of formula I, in which
U is methylene, and
A is pyridinyl or thiophenyl, such as e.g. thiophen-2-yl.

Another special embodiment (embodiment 5) of the compounds according to the present invention refers to those compounds of formula I, in which
R1 is (4-methoxy-phenyl)-methyl, or 4-methoxy-phenyl.

Another special embodiment (embodiment 6) of the compounds according to the present invention refers to those compounds of formula I, in which
R1 is 4-methoxy-phenyl.

Another special embodiment (embodiment 7) of the compounds according to the present invention refers to those compounds of formula I, in which
R1 is (4-methoxy-phenyl)-methyl, 2-hydroxy-phenyl, phenyl, 3-methoxycarbonyl-phenyl, or 4-methoxy-phenyl, 2-methoxy-phenyl, 4-bromo-phenyl, 2-bromo-phenyl, 2-fluoro-phenyl, or 2-(trifluoromethyl)-phenyl, or 2-chloro-phenyl, 4-bromo-phenyl, 2-methyl-phenyl.

Another special embodiment (embodiment 8) of the compounds according to the present invention refers to those compounds of formula I, in which
R1 is 4-methoxy-phenyl, 2-methoxy-phenyl, 4-bromo-phenyl, 2-bromo-phenyl, 2-fluoro-phenyl, or 2-(trifluoromethyl)-phenyl.

Another special embodiment (embodiment 9) of the compounds according to the present invention refers to those compounds of formula I, in which
R1 is 2-bromo-phenyl.

Another special embodiment (embodiment 10) of the compounds according to the present invention refers to those compounds of formula I, in which
R2 is methyl, methoxy, ethoxy, benzyloxy, chlorine, phenoxy, phenyl, 4-methoxy-phenyl, trifluoromethoxy, difluoromethoxy, methylthio, cyanomethyl, or —N(R22)R23, in which
R22 and R23 together and with inclusion of the nitrogen atom, to which they are attached, form a heterocyclic ring Het1, in which
Het1 is morpholin-4-yl, or 4N-methyl-piperazin-1-yl, and
R3 is hydrogen.

Another special embodiment (embodiment 11) of the compounds according to the present invention refers to those compounds of formula I, in which
R2 is methoxy, ethoxy, phenoxy, cyanomethyl, or —N(R22)R23, in which
R22 and R23 together and with inclusion of the nitrogen atom, to which they are attached, form a heterocyclic ring Het1, in which
Het1 is morpholin-4-yl, or 4N-methyl-piperazin-1-yl, and
R3 is hydrogen.

Another special embodiment (embodiment 11) of the compounds according to the present invention refers to those compounds of formula I, in which
R2 is attached in the meta position with respect to the binding position in which the phenyl ring is bonded to the amino group of the triazolophthalazine scaffold, and
R3 is attached in the meta or para position with respect to the binding position in which the phenyl ring is bonded to the amino group of the triazolophthalazine scaffold.

Another special embodiment (embodiment 14) of the compounds according to the present invention refers to those compounds of formula I, in which
R2 is attached in the para position with respect to the binding position in which the phenyl ring is bonded to the amino group of the triazolophthalazine scaffold, and
R3 is attached in the meta position with respect to the binding position in which the phenyl ring is bonded to the amino group of the triazolophthalazine scaffold.

A special group of the compounds according to the present invention refers to those compounds of formula I, in which
R1 is 4-methoxy-phenyl, 2-methoxy-phenyl, 4-bromo-phenyl, 2-bromo-phenyl, 2-fluoro-phenyl, or 2-(trifluoromethyl)-phenyl,
R2 is attached in the para or meta position with respect to the binding position in which the phenyl ring is bonded to the amino group of the triazolophthalazine scaffold, and is cyanomethyl, or —N(R22)R23, in which
R22 and R23 together and with inclusion of the nitrogen atom, to which they are attached, form a heterocyclic ring Het1, in which
Het1 is morpholin-4-yl, or 4N-methyl-piperazin-1-yl.

The compounds according to the invention can be prepared e.g. as described exemplarily as follows and according to the following specified reaction steps, or, particularly, in a manner as described by way of example in the following examples, or analogously or similarly thereto according to preparation procedures or synthesis strategies known to the person skilled in the art.

As shown in reaction scheme 1 below, compounds of formula I, in which R1, R2 and R3 have the abovementioned meanings can be obtained from corresponding compounds of formula II, in which X is a suitable leaving group, particularly chlorine, by reaction with corresponding aniline derivatives of formula III.

Said nucleophilic substitution reaction can be carried out as described in the following examples or as known to the skilled person; thus, depending on the reactivity of the reactants, it can be carried out by melting the reaction partners without solvent together or by reacting the reaction partners in a suitable solvent, such as e.g. N,N-dimethylformamide, in the presence of a suitable base, such as e.g. sodium hydride or potassium carbonate, at a temperature to allow the reaction to proceed (this may be e.g., depending on the reactants, ambient temperature, elevated temperature, or reflux temperature of the solvent used or, under appropriate conditions, beyond it), optionally under microwave irradiation.

Compounds of formula III are known, commercially available or can be obtained in a known manner. Compounds of formula II can be obtained as described later herein.

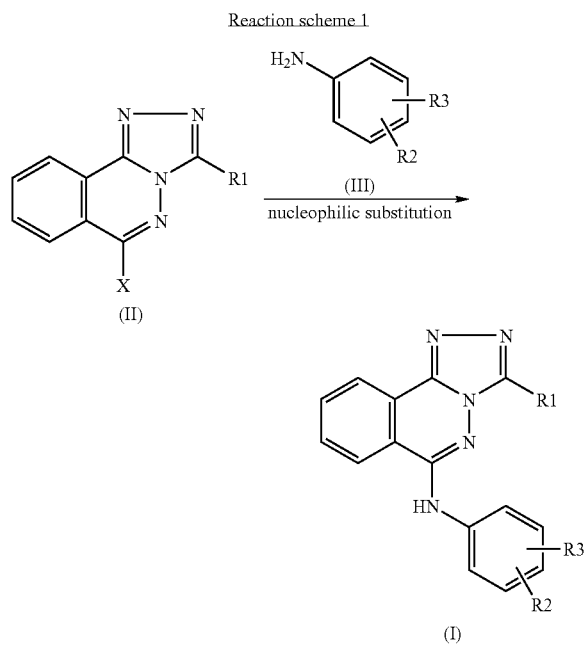

Starting compounds of formula II can be obtained as shown in reaction scheme 4 or as specified in the following examples; or they are art-known, such as e.g. from R. W. Carling et al., J. Med. Chem. Vol. 47, No. 7, 1807-1822 (2004), or they can be prepared according to known procedures or analogously or similarly to art-described compounds.

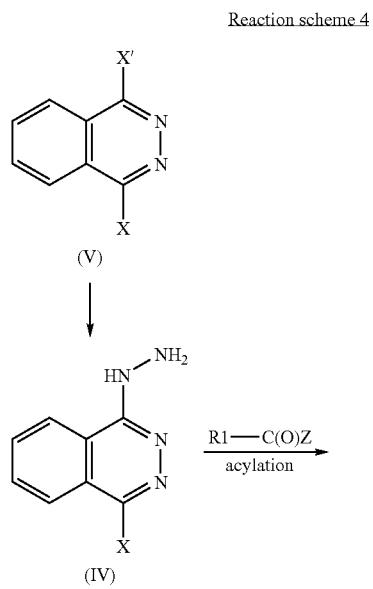

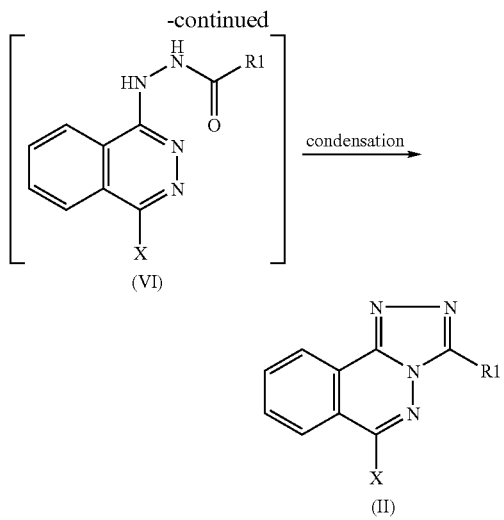

Compounds of formula II, in which R1 has the meanings mentioned above and X is a suitable leaving group, particularly chlorine, can be obtained from corresponding compounds of formula IV either in one step by cyclization reaction with corresponding compounds of formula R1-C(O)Z, in which Z is a suitable leaving group, such as e.g. chlorine; or in two steps via the isolatable intermediate of formula VI, which is accessible by acylation of compounds of formula IV and which can be further reacted to desired compounds of formula II by condensation reaction.

Said reactions can be carried out as described in the following examples, or under conditions known to the skilled person or analogously to art-known reactions similar thereto. Thus, the aforementioned one-step cyclization reaction can be carried out similarly as described in J. Med. Chem. Vol. 31, 1988, p. 1115, in a suitable solvent, such as e.g. toluene, pyridine or dioxane, in the presence of a suitable base (e.g. triethylamine) at elevated temperature or the reflux temperature of the solvent used.

Compounds of formula IV can be obtained by nucleophilic substitution of compounds of formula V, in which X and X' can be the same and are suitable leaving groups, particularly X and X' are both chlorine, and hydrazine.

Compounds of formulae R1-C(O)Z and V are known or can be obtained in a known manner.

Optionally, compounds of the formula I can be converted into their salts, or, optionally, salts of the compounds of the formula I can be converted into the free compounds.

It is moreover known to the person skilled in the art that if there are a number of reactive centers on a starting or intermediate compound it may be necessary to block one or more reactive centers temporarily by protective groups in order to allow a reaction to proceed specifically at the desired reaction center. A detailed description for the use of a large number of proven protective groups is found, for example, in "Protective Groups in Organic Synthesis" by T. Greene and P. Wuts (John Wiley & Sons, Inc. 1999, 3$^{rd}$ Ed.) or in "Protecting Groups (Thieme Foundations Organic Chemistry Series N Group" by P. Kocienski (Thieme Medical Publishers, 2000).

The substances of formula I according to the invention are isolated and purified in a manner known per se, for example by distilling off the solvent under reduced pressure and recrystallizing the residue obtained from a suitable solvent or subjecting it to one of the customary purification methods, such as, for example, column chromatography on a suitable support material.

Salts are obtained by dissolving the free compound in a suitable solvent (e.g. a ketone, such as acetone, methyl ethyl ketone or methyl isobutyl ketone, an ether, such as diethyl ether, tetrahydrofuran or dioxane, a chlorinated hydrocarbon, such as methylene chloride or chloroform, or a low-molecular-weight aliphatic alcohol, such as ethanol or isopropanol) which contains the desired acid or base, or to which the desired acid or base is then added. The salts are obtained by filtering, reprecipitating, precipitating with a nonsolvent for the addition salt or by evaporating the solvent. Salts obtained can be converted into the free compounds, which can in turn be converted into salts, by alkalization or by acidification. In this manner, pharmacologically unacceptable salts can be converted into pharmacologically acceptable salts.

Suitably, the conversions mentioned in this invention can be carried out analogously or similarly to methods which are familiar per se to the person skilled in the art.

The person skilled in the art knows on the basis of his/her knowledge and on the basis of those synthesis routes, which are shown and described within the description of this invention, how to find other possible synthesis routes for compounds of formula I. All these other possible synthesis routes are also part of this invention.

Having described the invention in detail, the scope of the present invention is not limited only to those described characteristics or embodiments. As will be apparent to persons skilled in the art, modifications, analogies, variations, derivations, homologisations and adaptations to the described invention can be made on the base of art-known knowledge and/or, particularly, on the base of the disclosure (e.g. the explicite, implicite or inherent disclosure) of the present invention without departing from the spirit and scope of this invention as defined by the scope of the appended claims.

The following examples serve to illustrate the invention further without restricting it. Likewise, further compounds of formula I, whose preparation is not explicitly described, can be prepared in an analogous or similar manner or in a manner familiar per se to the person skilled in the art using customary process techniques.

The compounds of formula I according to the present invention which are mentioned in the following examples as final compounds, as well as their salts are a preferred subject of the present invention.

In the examples, MS stands for mass spectrum, M for molecular ion in mass spectrometry, m.p. for melting point, EF for empirical formula, MW for molecular weight, calc. for calculated, fnd. for found, h for hours, and other abbreviations have their meanings customary per se to the skilled person.

EXAMPLES

Final Compounds 1. (4-Methoxyphenyl)-[3-(4-methoxyphenyl)-[1,2,4] triazolo[3,4-a]phthalazin-6-yl]-amine 5.0 g of 6-chloro-3-(4-methoxy-phenyl)-[1,2,4]triazolo[3, 4-a]phthalazine (compound B1), and 20 g p-anisidine are stirred at 170° C. for 5 h. The reaction mixture is diluted with 40 ml ethanol and the precipitate is filtered with suction. The solid is recrystallized from N,N-dimethylformamide to yield 5.2 g of the title compound. M.p.: 301-304° C.

EF:$C_{23}H_{19}N_5O_2$ (397.44) found:[M+1]398.2

Alternative Reaction Procedure I:

100 mg 6-chloro-3-(4-methoxy-phenyl)-[1,2,4]triazolo[3, 4-a]phthalazine (compound B1), 1-3 mmol of the appropriate aniline derivative and 30 mg potassium carbonate are stirred in 2.5 ml N,N-dimethylformamide at 140° C. for 4 h or at 200° C. for 10 min under microwave irradiation. The reaction mixture is diluted with dichloromethane/water or sodium hydroxide solution, the precipitate is filtered with suction, washed with water and recrystallized from N,N-dimethylformamide.

Alternative Reaction Procedure II:

2.5 mmol of the appropriate aniline derivative and 2.5 mmol sodium hydride (60%) in 2.5 ml N,N-dimethylformamide are treated with 100 mg 6-chloro-3-(4-methoxy-phenyl)-[1,2,4]triazolo[3,4-a]phthalazine (compound B1), at ambient temperature. After 10 min the reaction mixture is added to water, the precipitate is filtered with suction and the solid is recrystallized from N,N-dimethylformamide.

Alternative Work Up Procedure:

The product is purified by column chromatography via silica gel.

Starting from the corresponding starting materials described below (compounds B1 to B16) and the appropriate art-known aniline derivatives, the following compounds of Table 1 and further relevant, non-explicitly described similar compounds can be obtained analogously by using one of the procedures described above:

TABLE 1

| Example No. | chemical name | EF | MW | characterization |
|---|---|---|---|---|
| 2. | (3,4-Dimethoxy-phenyl)-[3-(4-methoxy-phenyl)-[1,2,4]triazolo[3,4-a]phthalazin-6-yl]-amine | C24 H21 N5 O3 | 427.47 | found: [M + 1] 428.3 |
| 3. | [3-(4-Methoxy-phenyl)-[1,2,4]triazolo[3,4-a]phthalazin-6-yl]-phenyl-amine | C22 H17 N5 O | 367.41 | found: [M + 1] 368.3 |
| 4. | (3-Benzyloxyphenyl)-[3-(4-methoxyphenyl)-[1,2,4]triazolo[3,4-a]phthalazin-6-yl]-amine | C29 H23 N5 O2 | 473.54 | m.p.: 260° C. |
| 5. | (4-Chlorophenyl)-[3-(4-methoxyphenyl)-[1,2,4]triazolo[3,4-a]phthalazin-6-yl]-amine | C22 H16 Cl N5 O | 401.86 | m.p.: 295° C. |
| 6. | (4'-Methoxybiphenyl-4-yl)-[3-(4-methoxyphenyl)-[1,2,4]triazolo[3,4-a]phthalazin-6-yl]-amine | C29 H23 N5 O2 | 473.54 | found: [M + 1] 474.4 |

TABLE 1-continued

| Example No. | chemical name | EF | MW | characterization |
|---|---|---|---|---|
| 7. | (3-Methoxyphenyl)-[3-(4-methoxyphenyl)-[1,2,4]triazolo[3,4-a]phthalazin-6-yl]-amine | C23 H19 N5 O2 | 397.44 | found: [M + 1] 398.3 |
| 8. | [3-(4-Methoxyphenyl)-[1,2,4]triazolo[3,4-a]phthalazin-6-yl]-(4-phenoxyphenyl)-amine | C28 H21 N5 O2 | 459.51 | m.p.: 275.5° C. |
| 9. | [3-(4-Methoxyphenyl)-[1,2,4]triazolo[3,4-a]phthalazin-6-yl]-(3-phenoxyphenyl)-amine | C28 H21 N5 O2 | 459.51 | found: [M + 1] 460.3 |
| 10. | (4-Benzyloxyphenyl)-[3-(4-methoxyphenyl)-[1,2,4]triazolo[3,4-a]phthalazin-6-yl]-amine | C29 H23 N5 O2 | 473.54 | m.p.: 297° C. |
| 11. | [3-(4-Methoxyphenyl)-[1,2,4]triazolo[3,4-a]phthalazin-6-yl]-p-tolyl-amine | C23 H19 N5 O | 381.44 | m.p.: 311° C. |
| 12. | (4-Ethoxyphenyl)-[3-(4-methoxyphenyl)-[1,2,4]triazolo[3,4-a]phthalazin-6-yl]-amine | C24 H21 N5 O2 | 411.47 | m.p.: 297.5° C. |
| 13. | [3-(4-Methoxyphenyl)-[1,2,4]triazolo[3,4-a]phthalazin-6-yl]-(4-morpholin-4-yl-phenyl)-amine | C26 H24 N6 O2 | 452.52 | m.p.: 314° C. |
| 14. | [3-(4-Methoxyphenyl)-[1,2,4]triazolo[3,4-a]phthalazin-6-yl]-(4-trifluoromethoxyphenyl)-amine | C23 H16 F3 N5 O2 | 451.41 | m.p.: 300° C. |
| 15. | {4-[3-(4-Methoxyphenyl)-[1,2,4]triazolo[3,4-a]phthalazin-6-ylamino]-phenyl}-acetonitrile | C24 H18 N6 O | 406.45 | m.p.: 295° C. |
| 16. | [3-(4-Methoxyphenyl)-[1,2,4]triazolo[3,4-a]phthalazin-6-yl]-(4-methylsulfanylphenyl)-amine | C23 H19 N5 O S | 413.5 | m.p.: 326° C. |
| 17. | (4-Morpholin-4-yl-phenyl)-[3-(4-phenoxyphenyl)-[1,2,4]triazolo[3,4-a]phthalazin-6-yl]-amine | C31 H26 N6 O2 | 514.59 | m.p.: 306° C. |
| 18. | [3-(4-Methoxyphenyl)-[1,2,4]triazolo[3,4-a]phthalazin-6-yl]-[4-(4-methylpiperazin-1-yl)-phenyl]-amine | C27 H27 N7 O | 465.56 | m.p.: 266° C. |
| 19. | 3-[6-(4-Morpholin-4-yl-phenylamino)-[1,2,4]triazolo[3,4-a]phthalazin-3-yl]-benzoic acid methyl ester | C27 H24 N6 O3 | 480.53 | NMR (d$_6$-DMSO, 200 MHz) 3.09-3.17 (m, 4H, 2CH$_2$), 3.72-3.83 (m, 4H, 2CH$_2$), 3.9 (s, 3H, OCH$_3$), 6.95-7.05 (m, 2H, H$^{Ar}$), 7.62-7.77 (m, 3H, H$^{Ar}$), 7.88-8.15 (m, 3H, H$^{Ar}$), 8.5-8.68 (m, 3H, H$^{Ar}$), 8.9 (s, 1H, H$^{Ar}$),, 9.29 (s, 1H, NH) |
| 20. | (4-Morpholin-4-yl-phenyl)-[3-(4-morpholin-4-yl-phenyl)-[1,2,4]triazolo[3,4-a]phthalazin-6-yl]-amine | C29 H29 N7 O2 | 507.6 | m.p.: 322° C. |
| 21. | [3-(4-Methoxy-benzyl)-[1,2,4]triazolo[3,4-a]phthalazin-6-yl]-(4-morpholin-4-yl-phenyl)-amine | C27 H26 N6 O2 | 466.55 | found: [M + 1] 467.3 |
| 22. | 4-[6-(4-Morpholin-4-yl-phenylamino)-[1,2,4]triazolo[3,4-a]phthalazin-3-yl]-benzoic acid methyl ester | C27 H24 N6 O3 | 480.53 | m.p.: 303° C. |
| 23. | (3-Ethoxyphenyl)-[3-(4-methoxyphenyl)-[1,2,4]triazolo[3,4-a]phthalazin-6-yl]-amine | C24 H21 N5 O2 | 411.47 | found: [M + 1] 412.3 |
| 24. | [3-(4-Methoxyphenyl)-[1,2,4]triazolo[3,4-a]phthalazin-6-yl]-(3-trifluoromethoxyphenyl)-amine | C23 H16 F3 N5 O2 | 451.41 | found: [M + 1] 452.3 |
| 25. | (4-Morpholin-4-ylphenyl)-(3-phenyl-[1,2,4]triazolo[3,4-a]phthalazin-6-yl)-amine | C25 H22 N6 O | 422.49 | m.p.: 306° C. |
| 26. | 2-[6-(4-Morpholin-4-yl-phenylamino)-[1,2,4]triazolo[3,4-a]phthalazin-3-yl]-phenol | C25 H22 N6 O2 | 438.49 | m.p.: 317° C. |
| 27. | (3,5-Dimethoxyphenyl)-[3-(4-methoxyphenyl)-[1,2,4]triazolo[3,4-a]phthalazin-6-yl]-amine | C24 H21 N5 O3 | 427.47 | m.p.: 218° C. |

TABLE 1-continued

| Example No. | chemical name | EF | MW | characterization |
|---|---|---|---|---|
| 28. | [3-(1,1-Difluoromethoxy)-phenyl]-[3-(4-methoxyphenyl)-[1,2,4]triazolo[3,4-a]phthalazin-6-yl]-amine | C23 H17 F2 N5 O2 | 433.42 | m.p.: 247° C. |
| 29. | (3,4-Diethoxyphenyl)-[3-(4-methoxyphenyl)-[1,2,4]triazolo[3,4-a]phthalazin-6-yl]-amine | C26 H25 N5 O3 | 455.52 | m.p.: 242.5° C. |
| 30. | [4-(1,1-Difluoromethoxy)-phenyl]-[3-(4-methoxyphenyl)-[1,2,4]triazolo[3,4-a]phthalazin-6-yl]-amine | C23 H17 F2 N5 O2 | 433.42 | m.p.: 294° C. |
| 31 | (4-Bromo-phenyl)-[3-(4-methoxy-phenyl)-[1,2,4]triazolo[3,4-a]phthalazin-6-yl]-amine | C22 H16 Br N5 O | 446.31 | m.p.: 314-316° C. |

Starting Compounds

B1. 6-Chloro-3-(4-methoxy-phenyl)-[1,2,4]triazolo[3,4-a]phthalazine 6.0 g (4-chloro-phthalazin-1-yl)-hydrazine (compound C1) are suspended in a mixture of 160 ml toluene and 18 ml triethylamine at 60° C. and treated with a solution of 6.0 g 4-methoxy-benzoyl chloride in 48 ml toluene. The mixture is stirred at 110° C. for 6 h, cooled to ambient temperature, filtered with suction and rinsed with toluene. The solid is recrystallized from N,N-dimethylformamide, the precipitate is washed with water and dried to yield 5.2 g of the title compound (m.p.: 192-193° C.).

EF:$C_{16}H_{11}ClN_4O$ (310.75) found:[M+1]311.2

Alternative Work Up Procedure:

The products can be purified by column chromatography via silica gel.

Starting from (4-chloro-phthalazin-1-yl)-hydrazine (compound C1) and the appropriate benzoic acid derivatives, the following compounds B2 to B15 can be obtained analogously to the procedure as described for compound B1 or B16.

B2. 6-Chloro-3-(2-methoxy-phenyl)-[1,2,4]triazolo[3,4-a]phthalazine

EF:$C_{16}H_{11}ClN_4O$ (310.75) found:[M+1]311.3 m.p.:136-140° C.

B3. 6-Chloro-3-(2-flouro-phenyl)-[1,2,4]triazolo[3,4-a]phthalazine

EF:$C_{15}H_8Cl\ F\ N_4$ (298.71) found:[M+1]299.0 m.p.:185-188° C.

B4. 6-Chloro-3-(2-bromo-phenyl)-[1,2,4]triazolo[3,4-a]phthalazine

EF:$C_{15}H_8Br\ ClN_4$ (359.61) found:[M+1]358.8 m.p.:197-200° C.

B5. 6-Chloro-3-(2-triflouromethyl-phenyl)-[1,2,4]triazolo[3,4-a]phthalazine

EF:$C_{16}H_8Cl\ F_3N_4$ (348.72) found:[M+1]348.9 m.p.:225-228° C.

B6. 6-Chloro-3-(2-methyl-phenyl)-[1,2,4]triazolo[3,4-a]phthalazine m.p.:189-191° C.

B7. 6-Chloro-3-(4-Bromo-phenyl)-[1,2,4]triazolo[3,4-a]phthalazine

EF:$C_{15}H_8Br\ ClN_4$ (359.61) found:[M+1]358.8 m.p.:191-195° C.

B8. 6-Chloro-3-(2-N,N-dimethylamino-phenyl)-[1,2,4]triazolo[3,4-a]phthalazine

EF:$C_{17}H_{14}ClN_5$ (323.79) found:[M+1]324.0 m.p.:180-185° C.

B9. 6-Chloro-3-(4-methoxybenzyl)-[1,2,4]triazolo[3,4-a]phthalazine

EF:$C_{17}H_{13}ClN_4O$ (324.77) m.p.:219.5° C.

B10. 4-(6-Chloro-[1,2,4]triazolo[3,4a]phthalazin-3-yl)-benzoic acid methyl ester EF:$C_{17}H_{11}ClN4O\ 2$(338.76) m.p.:211° C.

B11. 6-Chloro-3-(3-phenoxy-phenyl)-[1,2,4]triazolo[3,4-a]phthalazine

C21H13ClN4 O2 (372,82) m.p.:102° C.

B12. 3-(Chloro-[1,2,4]triazolo[3,4-a]phthalazin-3-yl-benzoic acid methyl ester

C17H11ClN4O2 (338,76 found:[M+1]339.3

B13. 2-(6-Chloro-[1,2,4]triazolo[3,4-a]phthalazin-3-yl-)phenol

C15H9ClN4O (296.72) :[M+1]297.4

B14. 3-(6-Chloro-[1,2,4]triazolo[3,4-a]phthalazin-3-yl-)phenol

C15H9ClN4O (296.72) :[M+1]297.3

B15. 6-(6-Chloro-3-(4-morpholin-4-yl-phenyl)-[1,2,4]triazolo[3,4-a]phthalazin $C_{19}H_{16}ClN_5O$ (365,83) m.p.:286° C.

B16. 6-Chloro-3-phenyl-[1,2,4]triazolo[3,4-a]phthalazine

Step 1:

2.5 g (4-chloro-phthalazin-1-yl)-hydrazine (compound C1) are suspended in 250 ml toluene and treated with a solution of 1.7 ml benzoic acid chloride in 50 ml toluene at reflux temperature. After 2 h the reaction mixture is cooled to ambient temperature and filtered with suction. The filtrate is concentrated under reduced pressure and the residue is recrystallized from N,N-dimethylformamide to yield 1.2 g of benzoic acid (4-chloro-2H-phthalazin-1-ylidene)-hydrazide.

EF:$C_{15}H_{11}ClFN_4O$ (298.73) found:[M+1]299.1

Step 2:

2.5 g benzoic acid (4-chloro-2H-phthalazin-1-ylidene)-hydrazide and 1 g triethylamine hydrochloride are suspended in 60 ml ethylene glycol and stirred at 130° C. for 3 h. The reaction mixture is cooled to ambient temperature and added to 600 ml water. The product is extracted with dichloromethane, the organic layer is dried with sodium sulphate and concentrated under reduced pressure. The residue is recrystallized from N,N-dimethylformamide to give the title compound.

EF:C15H9ClN4 (280.72) found:[M+1]281.2m.p.:162° C.

Alternative work up procedure: The products can be purified by column chromatography via silica gel.

C1. (4-Chloro-phthalazin-1-yl)-hydrazine 10 g commercially available dichlorophthalazine are added portionwise at 90° C. to a solution of 50 ml ethanol and 20 ml hydrazine hydrate. After 10 min the reaction mixture is cooled to ambient temperature, the precipitate is filtered with suction and rinsed with ethanol to yield 8.4 g of the title compound.

EF:C8H7ClN4 (194.62) found:[M+1]195.0

Commercial Applicability

The compounds according to the invention have useful pharmacological properties which make them industrially utilizable. As selective inhibitors of cyclic GMP-hydrolysing phosphodiesterases (cGMP-PDE inhibitors)—prefentially of type 2-, they are suitable on the one hand as therapeutics for conditions of pathologically enhanced endothelial activity and impaired endothelial barrier function such as septic shock, vascular edema, or diseases associated with unwanted neoangiogenesis. On the other hand, given the expression of PDE2 in neuronal tissue the compounds may also be useful in neurodegenerative conditions. In addition, PDE2 is expressed in human platelets and PDE2 inhibitors were shown to suppress platelet functions. In consequence, the compounds may be used as anti-thrombotics/platelet aggregation inhibitors. Furthermore, since PDE2 was shown in myocardium the compounds may afford a potential to protect against arrhythmias.

On account of their cGMP-PDE (preferentially PDE2) inhibiting properties, the compounds according to the invention can be employed in human and veterinary medicine as therapeutics, where they can be used, for example, for the treatment and prophylaxis of the following illnesses: (1) all conditions of pathologically enhanced endothelial activity/impaired endothelial barrier function such as multi-organ failure in particular acute respiratory distress syndrome (ARDS) in septic shock, pneumonia, acute and chronic airway disorders of varying origin (rhinitis, bronchitis, bronchial asthma, emphysema, COPD), angioedema, peripheral edema, cerebral edema for example traumatic or following stroke; (2) all conditions associated with pathologically enhanced neoangiogenesis such as all kinds of tumors (benign or malignant) which are associated with neoangiogenesis and all kinds of inflammatory diseases associated with neoangiogenesis for example disorders of the arthritis type (rheumatoid arthritis, rheumatoid spondylitis, osteoarthritis and other arthritic conditions), all forms of psoriasis, retinal blindness, bronchial asthma, inflammatory bowel disease, transplant rejection, allograft rejections, atherosclerosis; (3) all conditions for which platelet aggregation inhibition in conjunction with reduction of enhanced endothelial activation is desirable such as thrombembolic disorders and ischaemias covering myocardial infarct, cerebral infarct, transitory ischaemic attacks, angina pectoris, peripheral circulatory disorders, prevention of restenosis after thrombolysis therapy, percutaneous translumial angioplasty (PTA), percutaneous transluminal coronary angioplasty (PTCA) and bypass; (4) all types of impaired cognition in particular cognitive disorders such as mild cognitive disorder (MCI), Alzheimer's disease, Lewy-Body dementia, Parkinson's disease and cerebrovascular dementia; (5) in cardiac arrhythmias, and (6) osteoporosis, bone fracture and/or defect, bone in-growth.

The invention further relates to a method for the treatment of mammals, including humans, which are suffering from one of the above mentioned illnesses. The method is characterized in that a therapeutically active and pharmacologically effective and tolerable amount of one or more of the compounds according to the invention is administered to the ill mammal.

The invention further relates to a method for inhibiting PDE, particularly PDE2, comprising contacting said PDE with an effective amount of a compound according to the invention.

The invention further relates to a method for inhibiting PDE, particularly PDE2, comprising administering a pharmacologically active and therapeutically effective and tolerable amount of at least one compound according to the invention to a mammal in need of such inhibition.

The invention further relates to the compounds according to the invention for use in the treatment and/or prophylaxis of illnesses, especially the illnesses mentioned.

The invention further relates to the compounds according to the invention having PDE, particularly PDE2, inhibitory activity.

The invention also relates to the use of the compounds according to the invention for the production of pharmaceutical compositions which are employed for the treatment and/or prophylaxis of the illnesses mentioned.

The invention also relates to the use of the compounds according to the invention for the production of pharmaceutical compositions which are employed for the treatment and/or prophylaxis of PDE-, particularly PDE2-, associated diseases.

The invention furthermore relates to pharmaceutical compositions for the treatment and/or prophylaxis of the illnesses mentioned, which contain one or more of the compounds according to the invention.

The invention moreover relates to pharmaceutical compositions having PDE, particularly PDE2, inhibitory activity.

Additionally, the invention relates to an article of manufacture, which comprises packaging material and a pharmaceutical agent contained within said packaging material, wherein the pharmaceutical agent is therapeutically effective for antagonizing the effects of the cyclic nucleotide phosphodiesterase of type 2 (PDE2), ameliorating the symptoms of an PDE2-mediated disorder, and wherein the packaging material comprises a label or package insert which indicates that the pharmaceutical agent is useful for preventing or treating PDE2-mediated disorders, and wherein said pharmaceutical agent comprises one or more compounds of formula I according to the invention. The packaging material, label and package insert otherwise parallel or resemble what is generally regarded as standard packaging material, labels and package inserts for pharmaceuticals having related utilities.

The administration of the pharmaceutical compositions according to the invention may be performed in any of the generally accepted modes of administration available in the art. Illustrative examples of suitable modes of administration include intravenous, oral, nasal, parenteral, topical, transdermal and rectal delivery. Intravenous and oral delivery is preferred.

The pharmaceutical compositions are prepared by processes which are known per se and familiar to the person skilled in the art. As pharmaceutical compositions, the compounds according to the invention (=active compounds) are either employed as such, or preferably in combination with suitable pharmaceutical auxiliaries and/or excipients, e.g. in the form of tablets, coated tablets, capsules, caplets, suppositories, patches (e.g. as TTS), emulsions, suspensions, gels or solutions, the active compound content advantageously being between 0.1 and 95% and where, by the appropriate choice of the auxiliaries and/or excipients, a pharmaceutical administration form (e.g. a delayed release form or an enteric form) exactly suited to the active compound and/or to the desired onset of action can be achieved.

The person skilled in the art is familiar with auxiliaries or excipients which are suitable for the desired pharmaceutical formulations on account of his/her expert knowledge. In addition to solvents, gel formers, ointment bases and other active compound excipients, for example antioxidants, dispersants, emulsifiers, preservatives, solubilizers, colorants, complexing agents or permeation promoters, can be used.

For the treatment of disorders of the respiratory tract, the compounds according to the invention are preferably also administered by inhalation in the form of an aerosol; the aerosol particles of solid, liquid or mixed composition preferably having a diameter of 0.5 to 10 µm, advantageously of 2 to 6 µm.

Aerosol generation can be carried out, for example, by pressure-driven jet atomizers or ultrasonic atomizers, but advantageously by propellant-driven metered aerosols or propellant-free administration of micronized active compounds from inhalation capsules.

Depending on the inhaler system used, in addition to the active compounds the administration forms additionally contain the required excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of apparatuses are available with which aerosols of optimum particle size can be generated and administered, using an inhalation technique which is as right as possible for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhaler described in European Patent Application EP 0 505 321), using which an optimal administration of active compound can be achieved.

For the treatment of skin diseases, the compounds according to the invention are in particular administered in the form of those pharmaceutical compositions which are suitable for topical application. For the production of the pharmaceutical compositions, the compounds according to the invention (=active compounds) are preferably mixed with suitable pharmaceutical auxiliaries and further processed to give suitable pharmaceutical formulations. Suitable pharmaceutical formulations are, for example, powders, emulsions, suspensions, sprays, oils, ointments, fatty ointments, creams, pastes, gels or solutions.

The pharmaceutical compositions according to the invention are prepared by processes known per se. The dosage of the active compounds is carried out in the order of magnitude customary for PDE inhibitors. Topical application forms (such as ointments) for the treatment of dermatoses thus contain the active compounds in a concentration of, for example, 0.1-99%. The dose for administration by inhalation is customarily between 0.1 and 3 mg per day. The customary dose in the case of systemic therapy (p.o. or i.v.) is between 0.03 and 3 mg/kg per day.

Biological Investigations

Method for Measuring Inhibition of PDEs Activities

Abbreviations:

PDE: phosphodiesterase, PCR: polymerase chain reaction, RT-PCR: reverse transcription-polymerase chain reaction, dNTPs: deoxynucleoside triphosphates, RNA: ribonucleic acid, cDNA: complementary deoxyribonucleic acid, bp: basepairs, $(dT)_{15}$: pentadecathymidylic acid, ORF: open reading frame, GB no.: GenBank database accession number, rBV: recombinant baculovirus, wt: wild type, aa: aminoacid, UCR: upstream conserved region, PAA: polyacrylamide.

Aminoacids are abbreviated with the 1-character symbol: A for alanine, C for cysteine, D for aspartic acid, E for glutamic acid, F for phenylalanine, G for glycine, H for histidine, I for isoleucine, K for lysine, L for leucine, M for methionine, N for asparagine, P for proline, Q for glutamine, R for arginine, S for serine, T for threonine, V for valine, W for tryptophane, Y for tyrosine.

General Methods for Cloning Recombinant PDEs

RNA was purified from cell lines using the RNeasy Mini Kit from Qiagen. 1 µg RNA was reverse transcribed into single-stranded cDNA in a 20 µl reaction using Expand Reverse Transcriptase (Roche) with 50 pM of primer $(dT)_{15}$ and 1 mM dNTPs (both from Roche). 5 µl of cDNA were used as template for the subsequent PCR reaction. Human cDNAs from tissues were purchased from Clontech or Invitrogen. 1 µl was used for PCR reaction.

PCR was carried out in a Stratagene Robocycler 40 or in a MWG Primus 96 plus thermocycler. Typically, PCR was carried out with the Expand Lond Template PCR System from Roche in buffer 3 plus 0.75 mM $MgCl_2$, 0.3 µM each primer, 500 µM dNTPs.

PCR products were purified with the High Pure PCR Product Purification Kit (Roche) or from agarose gel with the QIAquick Gel Extraction kit from Qiagen, and cloned into the pCR2.1-TOPO vector from Invitrogen. The ORFs were subcloned in baculovirus expression vectors (transfer plasmids). The pCR-Bac and pVL vectors were from Invitrogen. The pBacPak vectors (pBP8 or pBP9) were from Clontech. Restriction endonucleases were from Roche and MBI Fermentas. Modifying enzymes and T4 DNA ligase were from New England Biolabs. DNA was sequenced by the company GATC GmbH (Konstanz, Germany, www.gatc.de) or in ALTANA Pharma's lab using an ABI PRISM 310 and the Big dye terminator cycle sequencing v2 chemistry (Applied Biosystem). Sequence analysis was performed with Hitachi Software DNASIS Version 2.5 or with Vector NTI 7. When necessary, in vitro mutagenesis was eventually performed with the QuickChange Site-Directed Mutagenesis Kit from Stratagene.

Cloning of Human PDE 2A3

The PDE2A3 (GB no. U67733) was amplified in 2 steps using PCR from brain cDNA. A N-terminal fragment was isolated using primers CP1PD2AS (5'-GAGGAGT-GATGGGGCAGGC-3') and PR9PD2M (5'-GCGAAGTGG-GAGACAGAAAAG-3'), a C-terminal fragment was isolated using primers PR7PD2AS (5'-GATCCTGAACATCCCT-GACG-3') and CP3PD2M (5'-GGGATCACTCAGCAT-CAAGGC-3'). The PCR products were cloned into the vector pCR2.1-Topo. The N-terminal fragment was first subcloned with EcoRI into pBluescript II KS (−), afterwards a Bst1107I/EcoRV fragment was exchanged with the corresponding restriction fragment from the C-terminal clone, to obtain a complete ORF. The ORF for the PDE2A3 was subcloned into pBP8 using XbaI and KpnI.

Expression of Recombinant PDE2

The rBV was prepared by means of homologous recombination in Sf9 insect cells. The expression plasmids were cotransfected with Bac-N-Blue (Invitrogen) or Baculo-Gold DNA (Pharmingen) using a standard protocol (Pharmingen). Wt virus-free recombinant virus supernatants were selected using plaque assay methods. After that, high-titre virus supernatants were prepared by amplifying 3 times. PDE2 was expressed in Sf21 cells by infecting $2\times10^6$ cells/ml with an MOI (multiplicity of infection) between 1 and 10 in serum-free SF900 medium (Life Technologies). Cells were cultured at 28° C., typically for 48 hours, after which they were pelleted for 5-10 min at 1000 g and 4° C. In spinner flasks, cells were cultured at a rotational speed of 75 rpm. The SF21 insect cells were resuspended, at a concentration of approx. $10^7$ cells/ml, in ice-cold (4° C.) homogenization buffer (20 mM Tris, pH 8.2, containing the following additions: 140 mM NaCl, 3.8 mM KCl, 1 mM EGTA, 1 mM $MgCl_2$, 1 mM β-mercaptoethanol, 2 mM benzamidine, 0.4 mM Pefablock, 10 µM leupeptin, 10 µM pepstatin A, 5 µM trypsin inhibitor) and disrupted by ultrasonication. The homogenate was then centrifuged for 10 min at 1000×g and the supernatant was stored at −80° C. until subsequent use (see below). The protein content was determined by the Bradford method (Bio-Rad, Munich) using BSA as standard. Integrity and size of recombinant proteins were analysed by western blot.

Measurement of Recombinant Human PDE2A3 Inhibition by SPA Technology

Recombinant human PDE2A3 activities were inhibited by the test samples in a modified SPA (scintillation proximity assay) test, supplied by Amersham Pharmacia Biotech (see procedural instructions "phosphodiesterase [3H]cAMP SPA enzyme assay, code TRKQ 7090"), carried out in 96-well microtitre plates (MTP's). The test volume is 100 µl and contains 20 mM Tris buffer (pH 7.4), 0.1 mg of BSA (bovine serum albumin)/ml, 5 mM $Mg^{2+}$, 0.5 µM cAMP (including about 50,000 cpm of [3H]cAMP), 5 µM cGMP (to activate PDE2A3), 2 µl of the respective substance dilution in DMSO and sufficient recombinant PDE (1000×g supernatant, see above) to ensure that 15-20% of the cAMP is converted under the said experimental conditions. After a preincubation of 5 min at 37° C., the reaction is started by adding the substrate (cAMP) and the assays are incubated for a further 15 min; after that, they are stopped by adding SPA beads (50 µl). In accordance with the manufacturer's instructions, the SPA beads had previously been resuspended in water and then diluted 1:3 (v/v); the diluted solution also contains 3 mM IBMX. After the beads have been sedimented (>30 min), the MTP's are analyzed in commercially available measuring appliances and the corresponding $IC_{50}$ values of the compounds for the inhibition of PDE activities are determined from the concentration-effect curves by means of non-linear regression.

Method to Assess Inhibition of Macromolecule Permeability of HUVEC Monolayers

The procedure to measure macromolecule permeability of endothelial cell monolayers followed the method described by Langeler & van Hinsbergh (1988) with modifications. Human umbilical vein endothelial cells were isolated from umbilical cords according to standard procedures (Jaffe et al. 1973) and cultured in endothelial cell basal medium (EBM) supplemented with 2% FCS, 0.5 ng/ml VEGF, 10 ng/ml bFGF, 5 ng/ml EGF, 20 ng/ml Long R3 IGF-1, 0.2 µg/ml hydrocortisone, 1 µg/ml ascorbic acid, 22.5 µg/ml heparin, 50 µg/ml gentamicin, 50 ng/ml amphotericin B (EGM2 purchased from Promocell GmbH, Heidelberg, Germany). At confluency, cells were trypsinized and replated at 73000 cells per well on 3 µm polycarbonate filter Transwell inserts (Costar GmbH, Bodenheim, Germany) precoated with 10 µg $cm^{-1}$ Fibronectin (Sigma, Taufkirchen, Germany). HUVECs were cultured in EGM2 (100 µl in the upper wells and 600 µl in the lower wells) over four days prior the experiments and medium was changed every other day. At the day of the experiment culture medium was replaced by M199 with 1% human serum albumin. Endothelial cells were preincubated with cyclic nucleotide modifiers (the selective PDE3 inhibitor motapizone, the selective PDE4 inhibitor RP73401, the cGMP generators ANP or SNP and PDE2 inhibitors) for 15 min. HUVECs were then stimulated with Thrombin (1 U $ml^{-1}$) (Sigma, Taufkichen, Germany) and horsh radish peroxidase (5 µg/ml) (Sigma, Taufkirchen, Germany) as the macromolecule marker protein was added to the upper wells. Following 1 h incubation time Transwells were removed and the activity of horsh radish peroxidase that penetrated the endothelial cell monolayer was measured in the lower wells with the 3,3',5,5'-tetramethylbenzidine liquid substrate system from Sigma (Taufkirchen, Germany).

Results

Representative inhibitory values [measured as $-\log IC_{50}$ (mol/l)] determined in the aforementioned assay follow from the following table A, in which the numbers of the compounds correspond to the numbers of the examples.

TABLE A

| Inhibition of PDE2 activity | |
|---|---|
| Compound | $-\log IC_{50}$ [mol/l] |
| 1 to 19, and 21 to 30 | The inhibitory values of these listed compounds lie in the range from 7.4 to 9.1 |

In parallel, compounds according to the invention can inhibit Thrombin-induced permeability of HUVEC monolayers for horsh radish peroxidase (HRP) as a macromolecule marker. Therefore, PDE2 inhibitors are suggested to improve the endothelial barrier function, which is impaired in numerous conditions such as acute respiratory distress syndrome (ARDS) or severe pneumonia. The system to measure these cellular effects of the PDE2 inhibitors observed the enzymological characteristics of PDE2 which exhibits a rather high Km for cAMP and the activity of which is activated by cGMP. The Thrombin-induced increase of HRP permeability was completely abolished by complete inhibition of PDE3 (10 µM Motapizone) and PDE4 (1 µM RP73401). However, in the additional presence of ANP (100 nM) or SNP (1 mM) to augment cGMP the inhibition by PDE3 and 4 inhibition of permeability was partially reversed. PDE2 inhibitors blocked the thrombin-stimulated HRP-permeability if 1 µM RP73401, 10 µM Motapizone, 100 nM ANP or 1 mM SNP were present indicating that ANP or SNP by generating cGMP activate PDE2. The concentration-dependent inhibition of HRP permeability at different concentrations was assessed from the percent inhibition in the presence and absence of the PDE2 inhibitors and in the presence of 1 µM RP73401, 10 µM Motapizone and 100 nM ANP. In the absence of PDE3 and 4 inhibition, ANP or SNP the PDE2 inhibitors showed very little effect in Thrombin-induced macromolecule hyperpermeability.

Inhibition of SNP- or ANP-Induced Permeability of HUVEC Monolayers:

HUVEC cells on 3 µm polycarbonate filters (Transwells) were preincubated with 1 µM RP73401 (to block PDE4) and 10 µM Motapizone (to block PDE3), 1 mM SNP or 100 nM ANP and test sample over 15 min and then stimulated with 1 U/ml thrombin. HRP passage into the lower wells was assessed after 60 min. RP73401 and Motapizone completely blocked thrombin-induced hyperpermeability, which was partially reversed by SNP and ANP.

Compounds according to this invention can inhibit the SNP- or ANP-induced permeability increase in a concentration-dependent fashion.

Representative inhibitory values [measured as $-\log IC_{50}$ (mol/l)] determined in the aforementioned assay follow from the following table B, in which the numbers of the compounds correspond to the numbers of the examples.

TABLE B

| Inhibition of SNP- or ANP-induced permeability | |
|---|---|
| Compound | $-\log IC_{50}$ [mol/l] |
| 2, 6 to 19, and 23 to 30 | The inhibitory values of these listed compounds lie in the range from 6.5 to 8.1 |

The invention claimed is:

1. A compound of formula I

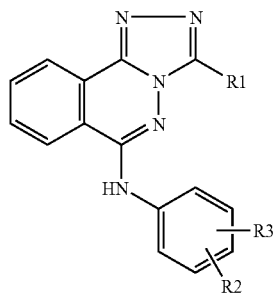

(I)

in which
R1 is —U-A, in which
U is a direct bond, or methylene (—CH$_2$—),
A is phenyl, pyridinyl, thienyl, or R11- and/or R111-substituted phenyl, in which
R11 is 1-4C-alkyl, halogen, trifluoromethyl, hydroxyl, 1-4C-alkoxy, completely or predominantly fluorine-substituted 1-4C-alkoxy, phenoxy, 1-4C-alkoxycarbonyl, morpholino, or di-1-4C-alkylamino,
R111 is 1-4C-alkoxy, halogen, hydroxyl, or 1-4C-alkyl,
R2 is hydrogen, 1-4C-alkyl, 1-4C-alkoxy, phenyl-1-4C-alkoxy, phenoxy, 3-7C-cycloalkoxy, 3-7C-cycloalkylmethoxy, halogen, trifluoromethyl, nitro, phenyl, R21-substituted phenyl, completely or predominantly fluorine-substituted 1-4C-alkoxy, 1-4C-alkylthio, cyano-1-4C-alkyl, or —N(R22)R23, in which
R21 is 1-4C-alkoxy, halogen or 1-4C-alkyl,
R22 and R23 together and with inclusion of the nitrogen atom, to which they are attached, form a heterocyclic ring Het1, in which
Het1 is optionally substituted by R24, and is a 3- to 7-membered monocyclic fully saturated heterocyclic ring radical comprising the nitrogen atom, to which R22 and R23 are bonded, and optionally one further heteroatom selected from the group consisting of nitrogen, oxygen and sulphur, in which
R24 is 1-4C-alkyl,
R3 is hydrogen, 1-4C-alkyl, 1-4C-alkoxy or halogen,
or a salt thereof.

2. A compound of formula I according to claim 1, in which
R1 is —U-A, in which
U is a direct bond, or methylene (—CH$_2$—), A is phenyl, pyridinyl, thienyl, dimethoxyphenyl, or R11-substituted phenyl, in which
R11 is methyl, tertbutyl, chlorine, fluorine, bromine, trifluoromethyl, hydroxyl, methoxy, ethoxy, trifluoromethoxy, phenoxy, methoxycarbonyl, morpholino, or dimethylamino,
R2 is hydrogen, 1-4C-alkyl, 1-4C-alkoxy, phenyl-1-4C-alkoxy, phenoxy, halogen, phenyl, R21-substituted phenyl, completely or predominantly fluorine-substituted 1-4C-alkoxy, 1-4C-alkylthio, cyano-1-4C-alkyl, or —N(R22)R23, in which
R21 is 1-4C-alkoxy,
R22 and R23 together and with inclusion of the nitrogen atom, to which they are attached, form a heterocyclic ring Het1, in which
Het1 is pyrrolidin-1-yl, piperidin-1-yl, morpholin-4-yl, thiomorpholin-4-yl, or 4N-(1-4C-alkyl)-piperazin-1-yl,
R3 is hydrogen or 1-4C-alkoxy,
or a salt thereof.

3. A compound of formula I according to claim 1, in which
R1 is —U-A, in which
U is a direct bond, or methylene (—CH$_2$—),
A is phenyl, 4-methoxy-phenyl, 2-methoxy-phenyl, 2-hydroxy-phenyl, 2-bromo-phenyl, 4-bromo-phenyl, 2-fluoro-phenyl, 2-(trifluoromethyl)-phenyl, 2-methyl-phenyl, 3-methoxy-phenyl, 3-bromo-phenyl, 3-fluoro-phenyl, 2-dimethylamino-phenyl, methoxycarbonyl, phenoxy, or 3-(trifluoromethyl)-phenyl,
R2 is hydrogen, 1-4C-alkyl, 1-4C-alkoxy, phenyl-1-4C-alkoxy, phenoxy, halogen, phenyl, R21-substituted phenyl, completely or predominantly fluorine-substituted 1-4C-alkoxy, 1-4C-alkylthio, cyano-1-4C-alkyl, or —N(R22)R23, in which
R21 is 1-4C-alkoxy,
R22 and R23 together and with inclusion of the nitrogen atom, to which they are attached, form a heterocyclic ring Het1, in which
Het1 is morpholin-4-yl, or 4N-(1-4C-alkyl)-piperazin-1-yl,
R3 is hydrogen or 1-4C-alkoxy,
or a salt thereof.

4. A compound of formula I according to claim 1, in which
R1 is 4-methoxy-phenyl, 2-methoxy-phenyl, 3-methoxyphenyl, 2-bromo-phenyl, 3-bromo-phenyl, 4-bromo-phenyl, 2-fluoro-phenyl, 3-fluoro-phenyl, 2-(trifluoromethyl)-phenyl, or 3-(trifluoromethyl)-phenyl;

R2 is hydrogen, methyl, methoxy, ethoxy, benzyloxy, chlorine, phenoxy, phenyl, 4-methoxy-phenyl, trifluoromethoxy, difluoromethoxy, methylthio, cyanomethyl, or —N(R22)R23, in which R22 and R23 together and with inclusion of the nitrogen atom, to which they are attached, form a heterocyclic ring Het1, in which Het1 is morpholin-4-yl, or 4N-methyl-piperazin-1-yl, R3 is hydrogen, methoxy or ethoxy, or a salt thereof.

5. A compound of formula I, selected from the group consisting of:

(4-Methoxyphenyl)-[3-(4-methoxyphenyl)-[1,2,4]triazolo[3,4-a]phthalazin-6-yl]-amine, (3,4-Dimethoxy-phenyl)-[3-(4-methoxy-phenyl)-[1,2,4]triazolo[3,4-a]phthalazin-6-yl]-amine,

[3-(4-Methoxy-phenyl)-[1,2,4]triazolo[3,4-a]phthalazin-6-yl]-phenyl-amine, (3-Benzyloxyphenyl)-[3-(4-methoxyphenyl)-[1,2,4]triazolo[3,4-a]phthalazin-6-yl]-amine, (4-Chlorophenyl)-[3-(4-methoxyphenyl)-[1,2,4]triazolo[3,4-a]phthalazin-6-yl]-amine, (4'-Methoxybiphenyl-4-yl)-[3-(4-methoxyphenyl)-[1,2,4]triazolo[3,4-a]phthalazin-6-yl]-amine, (3-Methoxyphenyl)-[3-(4-methoxyphenyl)-[1,2,4]triazolo[3,4-a]phthalazin-6-yl]-amine,

[3-(4-Methoxyphenyl)-[1,2,4]triazolo[3,4-a]phthalazin-6-yl]-(4-phenoxyphenyl)-amine,

[3-(4-Methoxyphenyl)-[1,2,4]triazolo[3,4-a]phthalazin-6-yl]-(3-phenoxyphenyl)-amine, (4-Benzyloxyphenyl)-[3-(4-methoxyphenyl)-[1,2,4]triazolo[3,4-a]phthalazin-6-yl]-amine,

[3-(4-Methoxyphenyl)-[1,2,4]triazolo[3,4-a]phthalazin-6-yl]-p-tolyl-amine, (4-Ethoxyphenyl)-[3-(4-methoxyphenyl)-[1,2,4]triazolo[3,4-a]phthalazin-6-yl]-amine,

[3-(4-Methoxyphenyl)-[1,2,4]triazolo[3,4-a]phthalazin-6-yl]-(4-morpholin-4-yl-phenyl)-amine,

[3-(4-Methoxyphenyl)-[1,2,4]triazolo[3,4-a]phthalazin-6-yl]-(4-trifluoromethoxyphenyl)-amine, {4-[3-(4-Methoxyphenyl)-[1,2,4]triazolo[3,4-a]phthalazin-6-ylamino]-phenyl}-acetonitrile,

[3-(4-Methoxyphenyl)-[1,2,4]triazolo[3,4-a]phthalazin-6-yl]-(4-methylsulfanylphenyl)-amine, (4-Morpholin-4-yl-phenyl)-[3-(4-phenoxyphenyl)-[1,2,4]triazolo[3,4-a]phthalazin-6-yl]-amine,

[3-(4-Methoxyphenyl)-[1,2,4]triazolo[3,4-a]phthalazin-6-yl]-[4-(4-methylpiperazin-1-yl)-phenyl]-amine, 3-[6-(4-Morpholin-4-yl-phenylamino)-[1,2,4]triazolo[3,4-a]phthalazin-3-yl]-benzoic acid methyl ester, (4-Morpholin-4-yl-phenyl)-[3-(4-morpholin-4-yl-phenyl)-[1,2,4]triazolo[3,4-a]phthalazin-6-yl]-amine,

[3-(4-Methoxy-benzyl)-[1,2,4]triazolo[3,4-a]phthalazin-6-yl]-(4-morpholin-4-yl-phenyl)-amine, 4-[6-(4-Morpholin-4-yl-phenylamino)-[1,2,4]triazolo[3,4-a]phthalazin-3-yl]-benzoic acid methyl ester, (3-Ethoxyphenyl)-[3-(4-methoxyphenyl)-[1,2,4]triazolo[3,4-a]phthalazin-6-yl]-amine,

[3-(4-Methoxyphenyl)-[1,2,4]triazolo[3,4-a]phthalazin-6-yl]-(3-trifluoromethoxyphenyl)-amine, (4-Morpholin-4-ylphenyl)-(3-phenyl-[1,2,4]triazolo[3,4-a]phthalazin-6-yl)-amine, 2-[6-(4-Morpholin-4-yl-phenylamino)-[1,2,4]triazolo[3,4-a]phthalazin-3-yl]-phenol, (3,5-Dimethoxyphenyl)-[3-(4-methoxyphenyl)-[1,2,4]triazolo[3,4-a]phthalazin-6-yl]-amine,

[3-(1,1-Difluoromethoxy)-phenyl]-[3-(4-methoxyphenyl)-[1,2,4]triazolo[3,4-a]phthalazin-6-yl]-amine, (3,4-Diethoxyphenyl)-[3-(4-methoxyphenyl)-[1,2,4]triazolo[3,4-a]phthalazin-6-yl]-amine,

[4-(1,1-Difluoromethoxy)-phenyl]-[3-(4-methoxyphenyl)-[1,2,4]triazolo[3,4-a]phthalazin-6-yl]-amine, (4-Bromo-phenyl)-[3-(4-methoxy-phenyl)-[1,2,4]triazolo[3,4-a]phthalazin-6-yl]-amine, and the salts of these compounds.

6. A pharmaceutical composition comprising one or more compounds of formula I according to claim 1 or a pharmaceutically acceptable salt thereof, together with a pharmaceutically acceptable excipient and/or auxiliary.

\* \* \* \* \*